(12) United States Patent
Gutierrez et al.

(10) Patent No.: US 10,188,284 B2
(45) Date of Patent: Jan. 29, 2019

(54) TEAR-FILM SENSING EYE-MOUNTABLE DEVICE

(71) Applicant: Verily Life Sciences LLC, Mountain View, CA (US)

(72) Inventors: Christian A. Gutierrez, San Jose, CA (US); Brian J. Kim, West Hills, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 28 days.

(21) Appl. No.: 15/231,108

(22) Filed: Aug. 8, 2016

(65) Prior Publication Data

US 2018/0035882 A1 Feb. 8, 2018

(51) Int. Cl.
| | | |
|---|---|---|
| *A61B 3/10* | (2006.01) | |
| *A61B 3/113* | (2006.01) | |
| *G02B 27/00* | (2006.01) | |
| *A61F 2/16* | (2006.01) | |
| *A61B 5/053* | (2006.01) | |

(Continued)

(52) U.S. Cl.
CPC .............. *A61B 3/101* (2013.01); *A61B 3/113* (2013.01); *A61B 5/053* (2013.01); *A61B 5/6821* (2013.01); *A61F 2/1624* (2013.01); *G02B 27/0093* (2013.01); *G02C 7/04* (2013.01); *G02C 7/083* (2013.01); *A61B 5/0002* (2013.01); *A61B 5/0537* (2013.01)

(58) Field of Classification Search
CPC ......... A61B 3/101; A61B 3/113; A61B 5/053; A61B 5/0537; A61B 5/14507; A61B 5/002; A61B 5/6821; A61F 2/1624; G02C 7/04; G02C 7/041; G02C 7/048; G02C 7/049; G02C 7/081; G02C 7/083
See application file for complete search history.

(56) References Cited

U.S. PATENT DOCUMENTS

| 7,018,040 B2 | 3/2006 | Blum et al. |
|---|---|---|
| 7,699,464 B2 | 4/2010 | Iuliano |

(Continued)

FOREIGN PATENT DOCUMENTS

| EP | 2 687 898 A1 | 1/2014 |
|---|---|---|
| JP | 2008 154857 A | 7/2008 |

(Continued)

OTHER PUBLICATIONS

Tobii Pro—Envision human behavior, http://www.tobiipro.com/, accessed Aug. 5, 2016, 5 pages.

(Continued)

*Primary Examiner* — Marin Pichler
(74) *Attorney, Agent, or Firm* — Christensen O'Connor Johnson Kindness PLLC

(57) ABSTRACT

An eye-mountable device includes an enclosure shaped to be removably mounted over a cornea. The device also includes a tear-film sensor system, including one or more tear-film-sensitive sensors, disposed within the enclosure. The one or more tear-film-sensitive sensors are disposed to measure an impedance of a tear-film in an eye of a user and to output a signal indicative of the impedance. A controller is also disposed within the enclosure and coupled to the tear-film sensor system to receive the signal and, in response to changes in the signal, actively control circuitry disposed in the eye-mountable device.

21 Claims, 8 Drawing Sheets

(51) Int. Cl.
  *G02C 7/04* (2006.01)
  *G02C 7/08* (2006.01)
  *A61B 5/00* (2006.01)

(56) References Cited

U.S. PATENT DOCUMENTS

| | | | |
|---|---|---|---|
| 7,926,940 | B2 | 4/2011 | Blum et al. |
| 8,636,358 | B2 | 1/2014 | Binder |
| 8,820,934 | B1* | 9/2014 | Ho .................. G02C 7/04 |
| | | | 351/159.02 |
| 8,880,139 | B1 | 11/2014 | Etzkorn et al. |
| 8,914,089 | B2 | 12/2014 | Abreu |
| 9,241,669 | B2 | 1/2016 | Pugh et al. |
| 2012/0268712 | A1 | 10/2012 | Egan et al. |
| 2014/0081178 | A1* | 3/2014 | Pletcher .................. G02C 7/04 |
| | | | 600/595 |
| 2015/0362750 | A1* | 12/2015 | Yeager .................. G02C 7/048 |
| | | | 351/209 |
| 2016/0091482 | A1* | 3/2016 | Bauer-Espindola ... G01N 27/02 |
| | | | 435/11 |

FOREIGN PATENT DOCUMENTS

| | | |
|---|---|---|
| WO | 90/07902 A1 | 1/1990 |
| WO | 2015/191301 A1 | 12/2015 |

OTHER PUBLICATIONS

SensoMotoric Instruments GmbH—Eye & Gaze Tracking Systems, http://www.smivision.com/en.html, accessed Aug. 5, 2016, 1 page.

LC Technologies, Inc.—Eye Tracking | Advanced Eye-Tracking Technology by LC Technologies, http://www.eyegaze.com, accessed Aug. 5, 2016, 1 page.

International Search Report and Written Opinion from the International Searching Authority dated Nov. 8, 2017, for International Application No. PCT/US2017/045370, filed Aug. 3, 2017, 17 pages.

* cited by examiner

TEAR-FILM SENSING EYE-MOUNTABLE DEVICE

TECHNICAL FIELD

This disclosure relates generally to the field of optics, and in particular but not exclusively, relates to contact lenses.

BACKGROUND INFORMATION

The tear-film coats the surface of the eye in a thin film comprised of three distinct layers. The mucosal layer is closest to the corneal surface, this is followed by the aqueous layer which is saline-like in composition, and the lipid layer forms the outermost tear-film layer and helps reduce evaporation from the eye surface. The thickness of the tear-film layer is on the order of 5 microns and is continuous across the corneal surface until sufficient evaporation has occurred to cause the film to break-up. Blinking aids in the replenishment and restoration of this film. Additionally, there are several areas of the precorneal eye anatomy where tears collect in larger volume: the lacrimal lake (which is a triangular region located by the tear duct), and the inferior tear meniscus (which exists along the lower eyelid). The inferior tear meniscus forms a region approximately 200-300 microns wide that extends up from the lower lid and represents a significant reservoir in terms of tear volume.

Accommodation is a process in which the eye adjusts its focal distance to maintain focus on objects of varying distance. Accommodation is a reflex action, but can be consciously manipulated. Accommodation is controlled by contractions of the ciliary muscle. The ciliary muscle encircles the eye's elastic lens and applies a force on the elastic lens during muscle contractions that change the focal point of the elastic lens.

As an individual ages, the effectiveness of the ciliary muscle degrades. Presbyopia is a progressive age-related loss of accommodative or focusing strength of the eye, which results in increased blur at near distances. This loss of accommodative strength with age has been well studied and is relatively consistent and predictable. Presbyopia affects nearly 1.7 billion people worldwide today (110 million in the United States alone) and that number is expected to rise as the world's population ages. Techniques and devices that can help individuals offset the effects of Presbyopia are increasingly in demand.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of an apparatus and method for a tear-film sensing eye-mountable device are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Described here is an eye-mountable device (or smart contact lens) that includes a tear-film sensor system which may be used for gaze detection. Gaze detection may be useful in an accommodating contact lens: a contact lens with an active lens system to adjust the optical power of the lens. If the accommodating contact lens can determine where the user is looking, the lens can adjust its optical power to assist the user and enhance what the user sees. This may be accomplished by measuring the impedance of the tear-film, and correlating these measurements to the location of the contact lens in the eye. The thickness of the tear-film is non-uniform across the surface of the eye, and the impedance changes with respect to the thickness of the film: the thicker the film, the lower the impedance, the thinner the film the higher the impedance. Thus, the location of the lens can be accurately determined relative to known tear-film reservoirs.

Figure 1:
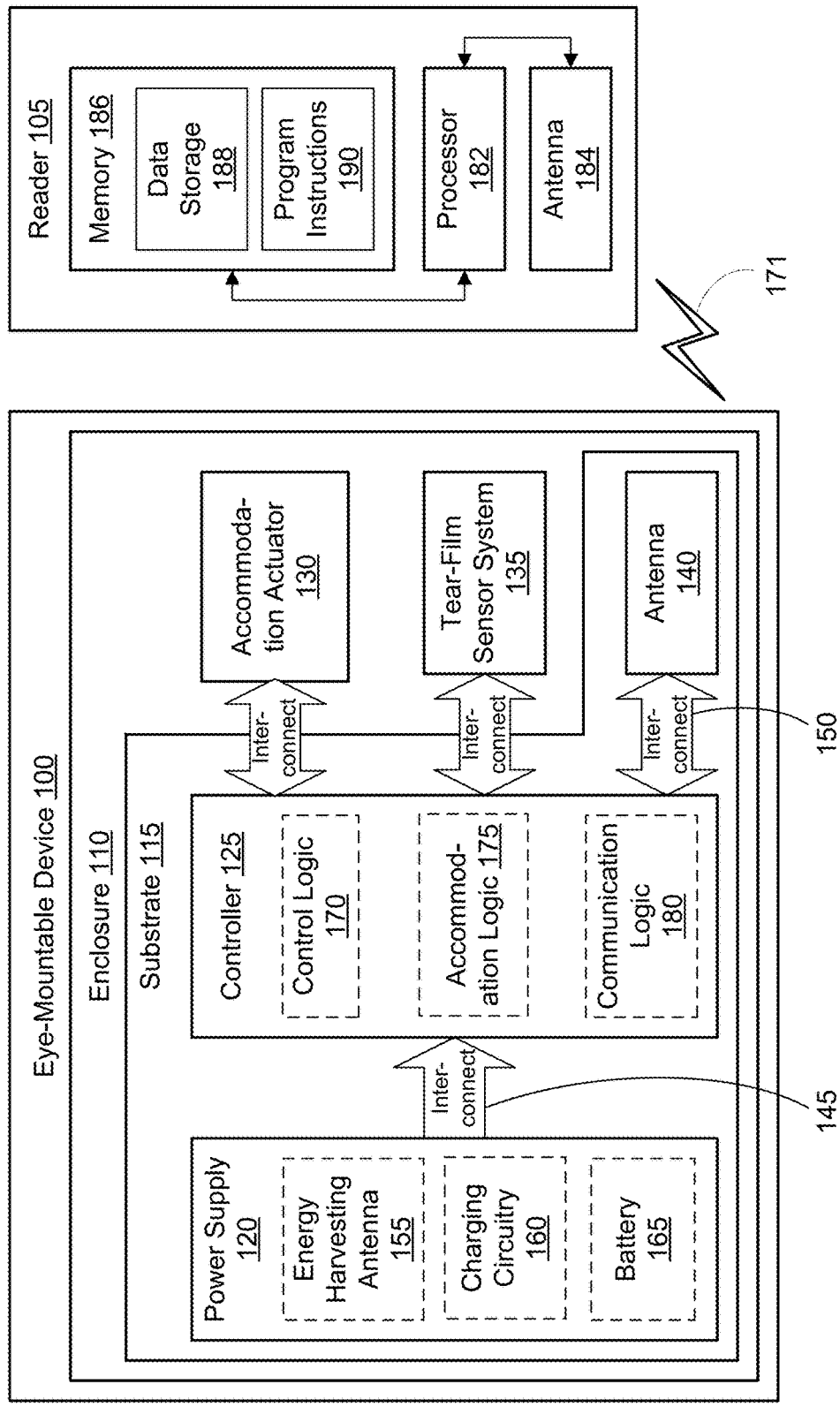
FIG. 1 is a functional block diagram of an eye-mountable device with a tear-film sensor system, in accordance with an embodiment of the disclosure.

FIG. 1 is a functional block diagram of eye-mountable device 100 with a tear-film sensor system 135, in accordance with an embodiment of the disclosure. In the depicted embodiment, eye-mountable device 100 includes an enclosure 110 formed to be contact-mounted to a corneal surface of an eye. A substrate 115 is embedded within or surrounded by enclosure 110 to provide a mounting surface for a power supply 120, a controller 125, an antenna 140, and various interconnects 145 and 150. The illustrated embodiment of power supply 120 includes an energy harvesting antenna 155, charging circuitry 160, and a battery 165. The illustrated embodiment of controller 125 includes control logic 170, accommodation logic 175, and communication logic 180. As shown, accommodation actuator 130 and tear-film sensor system 135 are disposed in the enclosure 110. Because eye-mountable device 100 includes electronics and is configured to be contact-mounted to an eye, it is also referred to herein as a contact lens, smart contact lens, or electronic contact lens.

Enclosure 110 in eye-mountable device 100 is configured to be removeably mounted over a cornea of a user's eye, and has a size and shape that permits eyelid motion when enclosure 110 is mounted. Tear-film sensor system 135 may including one or more tear-film-sensitive sensors disposed within the enclosure 110. The one or more tear-film-sensitive sensors are disposed to measure an impedance of a tear-film in an eye of a user, and to output a signal indicative of the impedance. Controller 125 is disposed within enclosure 110 and coupled to tear-film sensor system 135 to receive the signal and, in response to changes in the signal, actively control circuitry (e.g., accommodation actuator 130, antenna 140, power supply 120, etc.) disposed in eye-mountable device 100. In one embodiment, the one or more tear-film-sensitive sensors measure the impedance across a surface of eye-mountable device 100. In this embodiment, the impedance across the surface of eye-mountable device 100 is correlated with a location of eye-mountable device 100 in the eye of the user and a direction of user viewing.

Power supply 120 supplies operating voltages to the controller 125 and/or the accommodation actuator 130. Antenna 140 is operated by the controller 125 to communicate information to and/or from eye-mountable device 100. In the illustrated embodiment, antenna 140, controller 125, and power supply 120 are disposed on/in substrate 115, while tear-film sensor system 135 and accommodation actuator 130 are disposed in enclosure 110 (not in/on substrate 115). However, in other embodiments, the various pieces of circuitry and devices contained in eye-mountable device 100 may be disposed in/on substrate 115 or in enclosure 110, depending on the specific design of eye-mountable device 100. For example, in one embodiment, accommodation actuator 130 may be disposed on a transparent substrate.

Substrate 115 includes one or more surfaces suitable for mounting controller 125, power supply 120, and antenna 140. Substrate 115 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or silver nanowire mesh) can be patterned on substrate 115 to form circuitry, electrodes, etc. For example, antenna 140 can be formed by depositing a pattern of gold or another conductive material on substrate 115. Similarly, interconnects 145 and 150 can be formed by depositing suitable patterns of conductive materials on substrate 115. A combination of resists, masks, and deposition techniques can be employed to pattern materials on substrate 115. Substrate 115 can be a relatively rigid material, such as polyethylene terephthalate ("PET") or another material sufficient to structurally support the circuitry and/or electronics within enclosure 110. Eye-mountable device 100 can alternatively be arranged with a group of unconnected substrates rather than a single substrate 115. For example, controller 125 and power supply 120 can be mounted to one substrate 115, while antenna 140 is mounted to another substrate 115 and the two can be electrically connected via interconnects 150. Substrate 115 may also be a continuous piece of semiconductor, housing all or some of the aforementioned pieces of device architecture as integrated circuitry.

Substrate 115 can be shaped as a flattened ring with a radial width dimension sufficient to provide a mounting platform for the embedded electronic components. Substrate 115 can have a thickness sufficiently small to allow substrate 115 to be embedded in enclosure 110 without adversely influencing the profile of eye-mountable device 100. Substrate 115 can have a thickness sufficiently large to provide structural stability suitable for supporting the electronics mounted on it. For example, substrate 115 can be shaped as a ring with a diameter of about 10 millimeters, a radial width of about 1 millimeter (e.g., an outer radius 1 millimeter larger than an inner radius), and a thickness of about 50 micrometers. Substrate 115 can optionally be aligned with the curvature of the eye-mounting surface of eye-mountable device 100 (e.g., convex surface). For example, substrate 115 can be shaped along the surface of an imaginary cone between two circular segments that define an inner radius and an outer radius. In such an example, the surface of substrate 115 along the surface of the imaginary cone defines an inclined surface that is approximately aligned with the curvature of the eye mounting surface at that radius.

In the illustrated embodiment, power supply 120 includes a battery 165 to power the various embedded electronics, including controller 125. Battery 165 may be inductively charged by charging circuitry 160 and energy harvesting antenna 155. In one embodiment, antenna 140 and energy harvesting antenna 155 are independent antennae, which serve their respective functions of energy harvesting and communications. In another embodiment, energy harvesting antenna 155 and antenna 140 are the same physical antenna that are time shared for their respective functions of inductive charging and wireless communications with reader 105. Additionally or alternatively, power supply 120 may include a solar cell ("photovoltaic cell") to capture energy from incoming ultraviolet, visible, and/or infrared radiation. Furthermore, an inertial power scavenging system can be included to capture energy from ambient vibrations.

Charging circuitry 160 may include a rectifier/regulator to condition the captured energy for charging battery 165 or directly power controller 125 without battery 165. Charging circuitry 160 may also include one or more energy storage devices to mitigate high frequency variations in energy harvesting antenna 155. For example, one or more energy storage devices (e.g., a capacitor, an inductor, etc.) can be connected to function as a low-pass filter.

Controller 125 contains logic to choreograph the operation of the other embedded components. Control logic 170 controls the general operation of eye-mountable device 100, including providing a logical user interface, power control functionality, etc. Accommodation logic 175 includes logic for receiving signals from sensors monitoring the orientation of the eye, determining the current gaze direction, or focal distance of the user (e.g., tear-film sensor system 135), and manipulating accommodation actuator 130 (focal distance of the contact lens) in response to these physical cues. The auto-accommodation can be implemented in real-time based upon feedback from gaze tracking, or permit the user to select specific accommodation regimes (e.g., near-field accommodation for reading, far-field accommodation for regular activities, etc.). Communication logic 180 provides communication protocols for wireless communication with reader 105 via antenna 140. In one embodiment, communication logic 180 provides backscatter communication via antenna 140 when in the presence of an electromagnetic field 171 output from reader 105. In one embodiment, communication logic 180 operates as a smart wireless radio-frequency identification ("RFID") tag that modulates the impedance of antenna 140 for backscatter wireless communications. The various logic modules of controller 125 may be implemented in software/firmware executed on a general purpose microprocessor, in hardware (e.g., application specific integrated circuit), or a combination of both.

Eye-mountable device 100 may include various other embedded electronics and logic modules. For example, a light source or pixel array may be included to provide visible feedback to the user. An accelerometer or gyroscope may be included to provide positional, rotational, directional or acceleration feedback information to controller 125.

The illustrated embodiment also includes reader 105 with a processor 182, an antenna 184, and memory 186. Memory 186 in reader 105 includes data storage 188 and program instructions 190. As shown reader 105 may be disposed outside of eye-mountable device 100, but may be placed in its proximity to charge eye-mountable device 100, send instructions to eye-mountable device 100, and/or extract data from eye-mountable device 100. In one embodiment, reader 105 may resemble a conventional contact lens holder that the user places eye-mountable device 100 in at night to charge, extract data, clean the lens, etc.

External reader 105 includes an antenna 184 (or group of more than one antennae) to send and receive wireless signals 171 to and from eye-mountable device 100. External reader 105 also includes a computing system with a processor 182 in communication with a memory 186. Memory 186 is a non-transitory computer-readable medium that can include, without limitation, magnetic disks, optical disks, organic memory, and/or any other volatile (e.g., RAM) or non-volatile (e.g., ROM) storage system readable by the processor 182. Memory 186 can include a data storage 188 to store indications of data, such as data logs (e.g., user logs), program settings (e.g., to adjust behavior of eye-mountable device 100 and/or external reader 105), etc. Memory 186 can also include program instructions 190 for execution by processor 182 to cause the external reader 105 to perform processes specified by the instructions 190. For example, program instructions 190 can cause external reader 105 to provide a user interface that allows for retrieving information communicated from eye-mountable device 100 or allows transmitting information to eye-mountable device 100 to program or otherwise select operational modes of eye-mountable device 100. External reader 105 can also include one or more hardware components for operating antenna 184 to send and receive wireless signals 171 to and from eye-mountable device 100.

External reader 105 can be a smart phone, digital assistant, or other portable computing device with wireless connectivity sufficient to provide the wireless communication link 171. External reader 105 can also be implemented as an antenna module that can be plugged in to a portable computing device, such as in an embodiment where the communication link 171 operates at carrier frequencies not commonly employed in portable computing devices. In some instances, external reader 105 is a special-purpose device configured to be worn relatively near a wearer's eye to allow the wireless communication link 171 to operate with a low power budget. For example, the external reader 105 can be integrated in a piece of jewelry such as a necklace, earring, etc. or integrated in an article of clothing worn near the head, such as a hat, headband, etc.

Figure 2A:
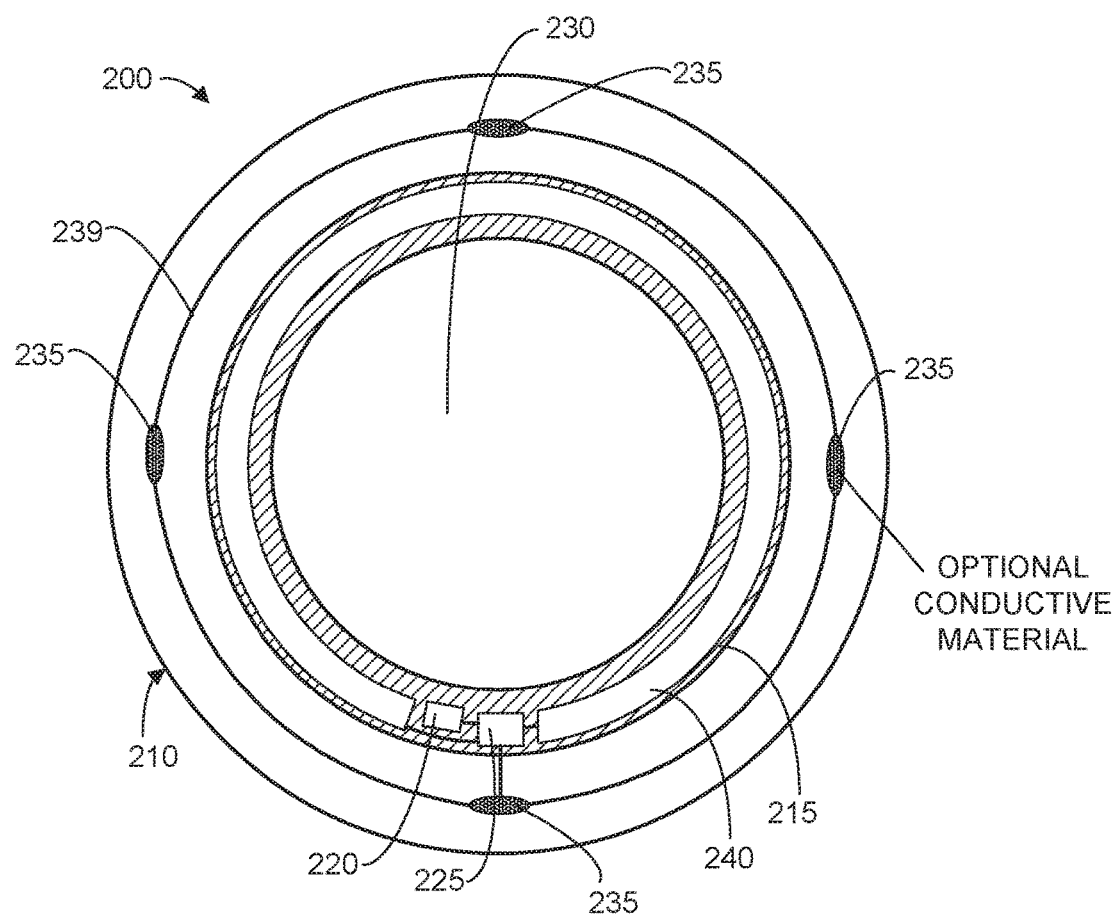
FIG. 2A is a top view of the eye-mountable device of FIG. 1, in accordance with an embodiment of the disclosure.

FIG. 2A is a top view of eye-mountable device 200 (which is an embodiment of the eye-mountable device 100 of FIG. 1). The illustrated embodiment of eye-mountable device 200 includes: an enclosure 210, a substrate 215, a power supply 220, a controller 225, an accommodation actuator 230, a tear-film sensor system (including individual tear-film-sensitive sensors 235), interconnects 239, and an antenna 240. It should be appreciated that FIGS. 2A and 2B are not necessarily drawn to scale, but have been illustrated for purposes of explanation only in describing the arrangement of the example eye-mountable device 200.

Eye-mountable device 200 is a circular contact lens with a tear-film sensor system, including one or more tear-film-sensitive sensors 235. The tear-film sensor system is disposed within eye-mountable device 200 and coupled to output a signal in response to a change in tear-film thickness in an eye of the user. Accommodation actuator 230 is circular and disposed in eye-mountable device 200 to optically align with a cornea of the user when eye-mountable device 200 is mounted in an eye of the user. The one or more tear-film-sensitive sensors 235 are disposed around a periphery of eye-mountable device 200 such that light entering the eye of the user is substantially unobstructed by the one or more tear-film-sensitive sensors 235 when the enclosure 210 is mounted over the cornea. In the depicted embodiment, tear-film sensor system includes at least two tear-film-sensitive sensors 235, and measures the impedance between the at least two tear-film-sensitive sensors 235 disposed on opposite sides of eye-mountable device 200. In the illustrated embodiment, the tear-film-sensitive sensors 235 are exposed electrodes which may include metal or conductive polymer. Controller 225 is disposed in eye-mountable device 200 and electrically coupled to the tear-film sensor system and the accommodation actuator 230. Controller 225 includes logic that when executed by controller 225 causes controller 225 to perform operations including: (1) controlling one or more other pieces of circuitry disposed in eye-mountable device 200 in response to the signal from the tear-film sensor system; and (2) electrically manipulating accommodation actuator 230 to change an optical power of the contact lens. In one embodiment, controlling the one or more other pieces of circuitry includes manipulating accommodation actuator 230 in response to the signal.

In the depicted embodiment, interconnects 239 extend between one or more tear-film sensitive sensors 235 and may include many small wires to individually transmit signals from one or more tear-film-sensitive sensors 235 to controller 225. Power supply 220 is also coupled to controller 225, accommodation actuator 230, and antenna 240 to supply power to controller 225, supply power to accommodation actuator 230, and/or receive power from antenna 240.

Figure 2B:
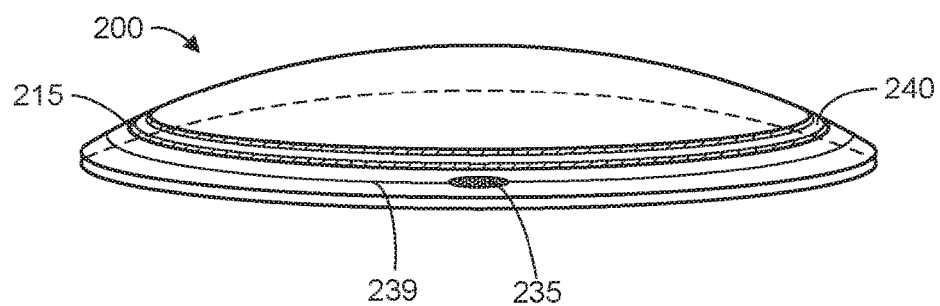
FIG. 2B is a perspective view of the eye-mountable device of FIG. 2A, in accordance with an embodiment of the disclosure.

FIG. 2B is a perspective view of eye-mountable device 200 of FIG. 2A, in accordance with an embodiment of the disclosure. Enclosure 210 of eye-mountable device 200 is shaped as a curved disk. As shown, to facilitate contact-mounting, the enclosure 210 can have a concave surface configured to adhere ("mount") to a moistened corneal surface (e.g., by capillary forces with a tear-film coating the corneal surface). Additionally, the eye-mountable device 200 may be adhered by a vacuum force between the corneal surface and enclosure 210 due to the concave curvature. While mounted with the concave surface against the eye, the outward-facing surface of the enclosure 210 can have a convex curvature that is formed to not interfere with eye-lid motion while the eye-mountable device 200 is mounted to the eye.

Enclosure 210 may be a substantially transparent material to allow incident light to be transmitted to the eye while eye-mountable device 200 is mounted to the eye. Enclosure 210 may be a biocompatible material similar to those employed to form vision correction and/or cosmetic contact lenses in optometry, such as a polymeric material like polyethylene terephthalate ("PET"), polymethyl methacrylate ("PMMA"), polyhydroxyethylmethacrylate ("poly-HEMA"), a hydrogel, silicon based polymers (e.g., fluoro-silicon acrylate) combinations of these, or otherwise.

Figure 3A:
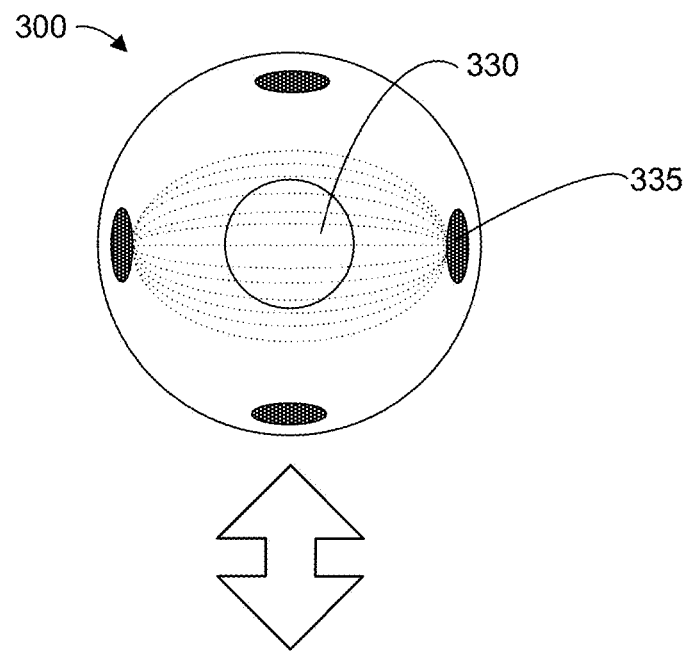
FIGS. 3A-3B illustrate a tear-film sensor system measuring impedance, in accordance with an embodiment of the disclosure.
Figure 3B:
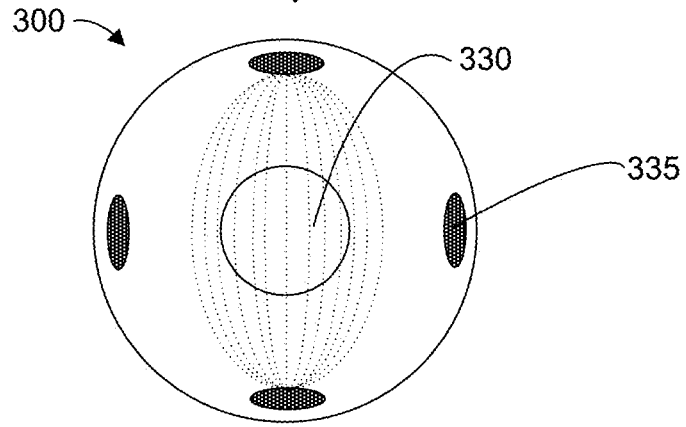

FIGS. 3A-3B illustrate a tear-film sensor system (included in eye-mountable device 300) measuring impedance, in accordance with an embodiment of the disclosure. FIGS. 3A-3B are simplified depictions of the eye-mountable device 200 illustrated in FIGS. 2A-2B. As shown the tear-film sensor system has four tear-film-sensitive sensors 335 disposed on opposite sides of the device from one another. Disposed in the center of eye-mountable device 300 is accommodation actuator 330 which may change its optical power in repose to a signal derived from the tear-film sensitive sensors 335. Also shown in FIGS. 3A-3B are alternating current (AC) electric field lines spanning the center of eye-mountable device 300. In the depicted embodiment, the tear-film sensor system applies an AC voltage across the surface of the device and measures an impedance across eye-mountable device 300. The impedance is proportional to a tear-film thickness. In FIG. 3A the AC waveform is applied from the right tear-film-sensitive sensor 335 to the left tear-film-sensitive sensor 335. This electric field distribution may provide information about the position of the eye as measured by the eye-mountable device 300, when eye-mountable device 300 and the user's eye move in unison. In FIG. 3B the AC waveform is applied from the top tear-film-sensitive sensor 335 to the bottom tear-film-sensitive sensor 335. This electric field distribution may provide information about the vertical location of eye-mountable device 300 in the eye of the user. In the depicted embodiments, eye-mountable device 300 alternates between applying a vertically oriented electric field and a horizontally oriented electric field. This may allow eye-mountable device 300 to determine its horizontal and vertical position in the eye of the user.

Figure 4A:
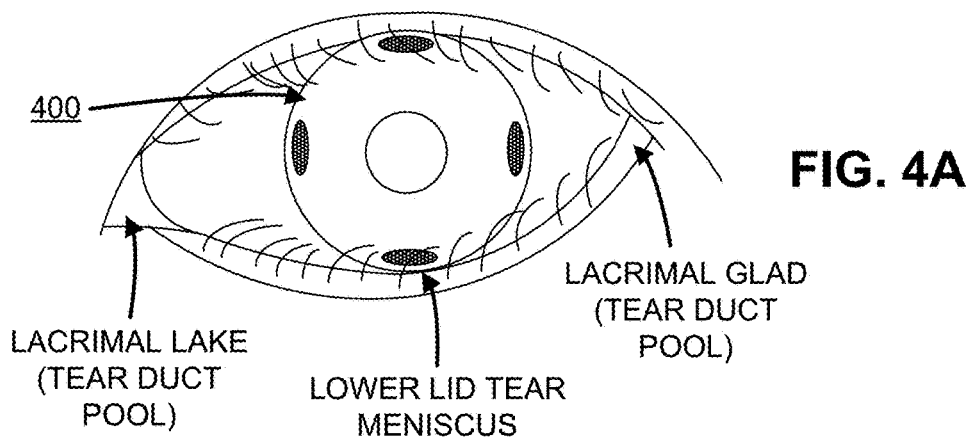
FIGS. 4A-4E illustrate use cases for the eye-mountable device of FIG. 1, in accordance with several embodiments of the disclosure.

FIGS. 4A-4E illustrate use cases for the eye-mountable device of FIGS. 2A-2B, in accordance with several embodiments of the disclosure. FIG. 4A shows a cartoon of a human eye with eye-mountable device 400 disposed in the eye. It is worth noting that the human eye has a tear-film disposed over the surface of the eye. This tear-film may also extend over the surface of worn contact lenses. But the tear-film is not evenly distributed over the surface of the eye. Due to the effects of gravity and location of glands, the tear-film is thicker closer to the edges and bottom of the eye. As shown the lacrimal lake (tear duct pool) is disposed on the inside edge of the eye (i.e., the side of the eye closest to the nose). The lacrimal gland is disposed on the outside edge of the eye (i.e., the side of the eye furthest from the nose). Similarly, the lower lid tear meniscus is formed at the bottom of the eye. All of these locations have a thicker tear-film and subsequently a lower impedance when an AC electric field is applied across them.

FIGS. 4B-4E show simplified versions of the eye depicted in FIG. 4A, as well as the location of eye-mountable device 400 in the eye relative to the various pools and glands.

Figure 4B:
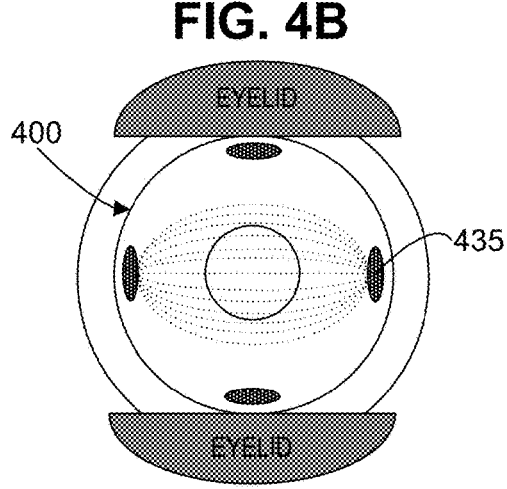

In FIG. 4B eye-mountable device 400 is disposed in the center of the eye. This results in a relatively high impedance measurement due to the thin volumetric conduction path through the tear film between tear-film-sensitive sensors 435 relative to thick parts of the tear-film (e.g., near the lower lid or edges of the eye).

Figure 4C:
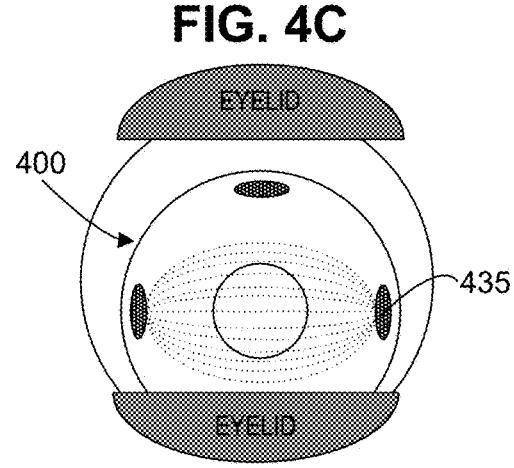

FIG. 4C shows the eye looking down; subsequently the bottom tear-film-sensitive sensor 435 is occluded by the lower lid. Additionally, the lateral tear-film-sensitive sensors 435 are moved closer to the lower lid tear meniscus where the volumetric conduction path is greater creating a correspondingly lower (and unique) impedance value which may be associated with a downward gaze.

Figure 4D:
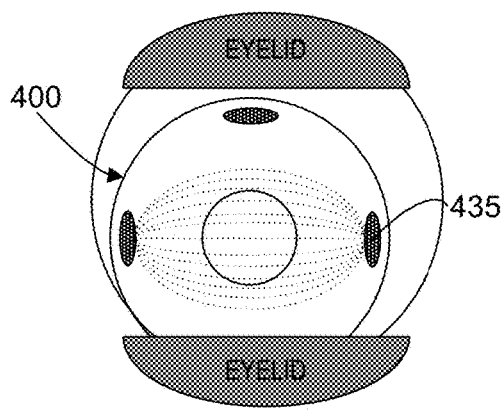

FIG. 4D illustrates the eye looking in (sideways gaze). This may result in a higher impedance measurement than when the eye looks down, but a lower impedance measurement than when the eye is looking straight ahead (because the left tear-film-sensitive sensor 435 is disposed proximate to the lacrimal lake).

Figure 4E:
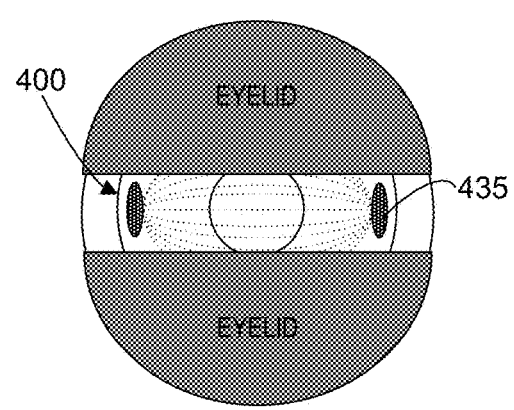

FIG. 4E shows the eye squinting. This may result in an impedance measurement that is lower than other impedance measurements for the gazes depicted, because the impedance measured between the right and left tear-film-sensitive sensors 435 is lower as a result of the greater volumetric conduction path of the tear film in proximity to the lower lid tear meniscus.

Figure 5:
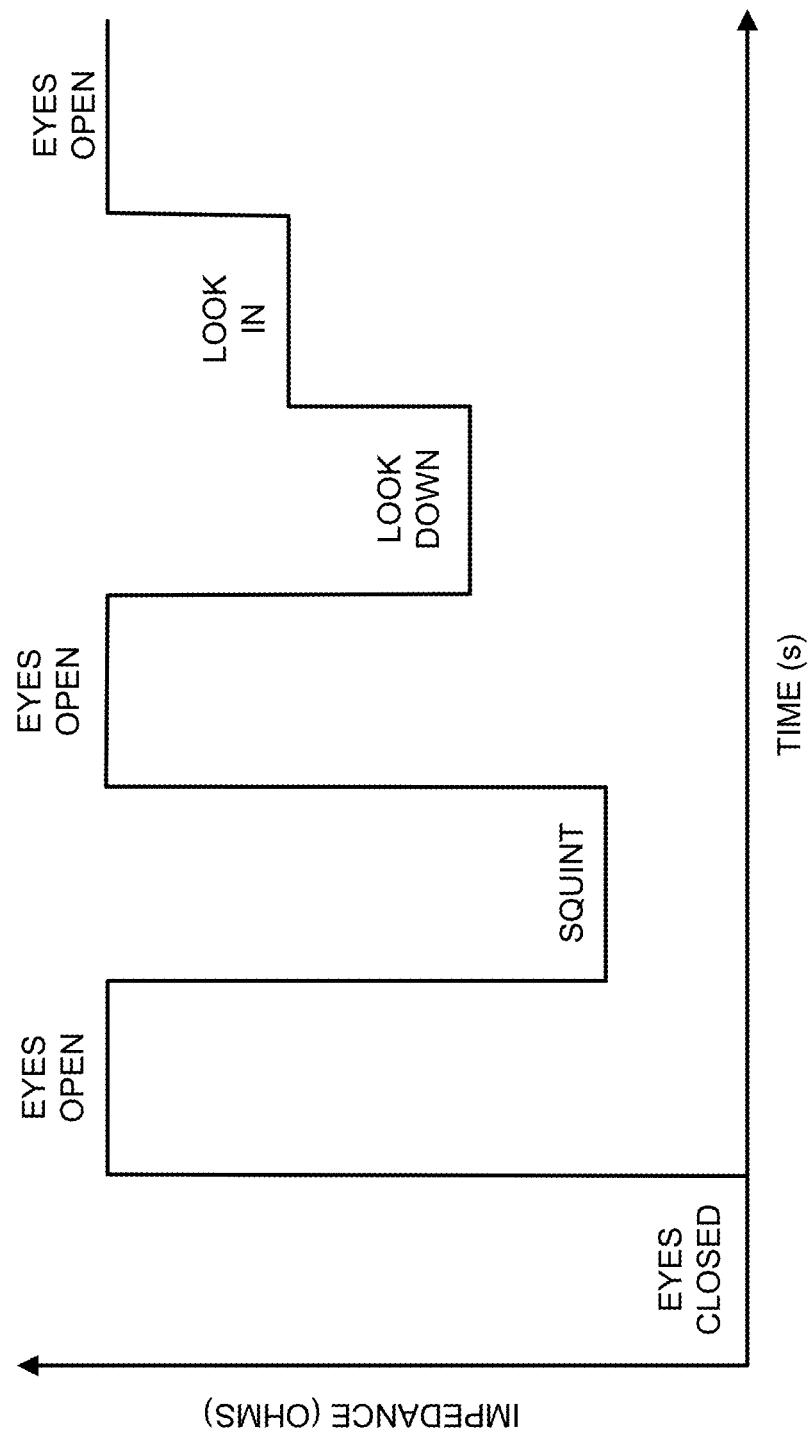
FIG. 5 is an illustration of idealized impedance measurements for the use cases in FIGS. 4A-4E, in accordance with an embodiment of the disclosure.

FIG. 5 is an illustration of idealized impedance measurements for the use cases in FIGS. 4A-4E, in accordance with an embodiment of the disclosure. One skilled in the art will appreciate that FIG. 5 merely shows example impedance measurements. In the real world, impedance measurements may be different depending on the individual's eye, and the system used. For example, looking down may be associated with a higher impedance value than looking sideways/in or vice versa. Further the measurements may be subject to interference or distortion.

In the depicted embodiment, when the eyes are closed, the impedance may be very low because the tear-film-sensitive sensors are submerged in a thick layer of tear-film under the eyelids. Next when the eyes open the impedance may increase rapidly because the tear-film-sensitive sensors have a much thinner tear film layer covering them, decreasing the volumetric conduction path between tear-film-sensitive sensors. When the eyes squint, the impedance may drop again (but not as far as when the eyes are closed) because of the increased volumetric conduction path through the tear film between the tear-film-sensitive sensors. Next when the eyes open, the impedance may once again increase to the eyes-open value. When the user looks down the impedance decreases due to the tear-film-sensitive sensors moving closer to a pool of tear-film formed by the lower lid tear meniscus. Similarly, looking in changes (raises) the impedance measurement because the proximity of the tear-film-sensitive sensors changed relative to pools of tears.

Since the impedance values vary as the eye changes locations, values (or value ranges) may be associated with the eye looking in a particular direction. In one embodiment, a controller in the eye-mountable device may manipulate an accommodation actuator in response to the gaze directions. The accommodation actuator may change its optical power to aid the user. For example, if the user is looking down, it is likely the user is focusing on something a short distance away such as a book. The accommodation actuator may respond by enhancing near-sighted vision. Conversely, if the controller detects that the user is squinting, it is likely that the user is looking far away. Accordingly, the accommodation actuator may respond by enhancing far-sighted vision.

FIGS. 6A-6E illustrate several configurations of eye-mountable device 600 with a tear-film sensor system, in accordance with several embodiments of the disclosure. It should be noted that other pieces of device architecture are present but not depicted to avoid obscuring certain aspects of the disclosure. Further accommodation actuator 630 is depicted in the center of the device for a frame of reference, but in other embodiments, accommodation actuator 630 may not be present.

Figure 6A:
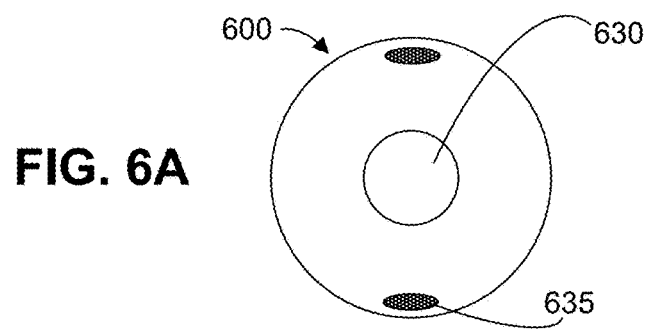
FIGS. 6A-6E illustrate several configurations of an eye-mountable device with a tear-film sensor system, in accordance with several embodiments of the disclosure.

FIG. 6A shows two tear-film-sensitive sensors 635 disposed on opposite sides of eye-mountable device 600. Accordingly, FIG. 6A has an even number of tear-film-sensitive sensors 635 spaced evenly around the periphery of eye-mountable device 600.

Figure 6B:
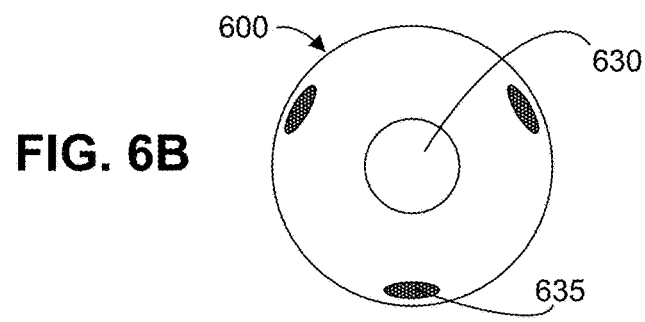

FIG. 6B shows three tear-film-sensitive sensors 635 disposed around eye-mountable device 600. In other words, FIG. 6B has an odd number of tear-film-sensitive sensors 635 spaced evenly around the periphery of eye-mountable device 600.

Figure 6C:
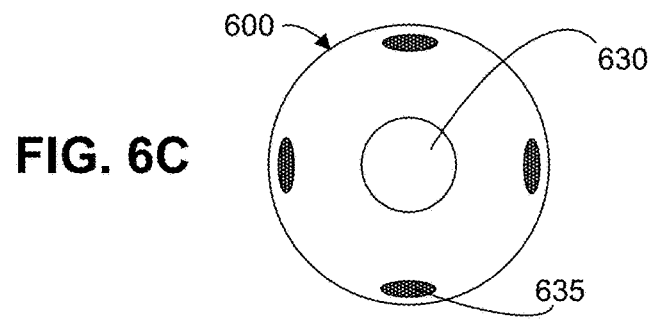

FIG. 6C shows four tear-film-sensitive sensors 635 disposed on opposite sides of eye-mountable device 600. Accordingly, FIG. 6C has an even number of tear-film-sensitive sensors 635 spaced evenly around the periphery of eye-mountable device 600.

Figure 6D:
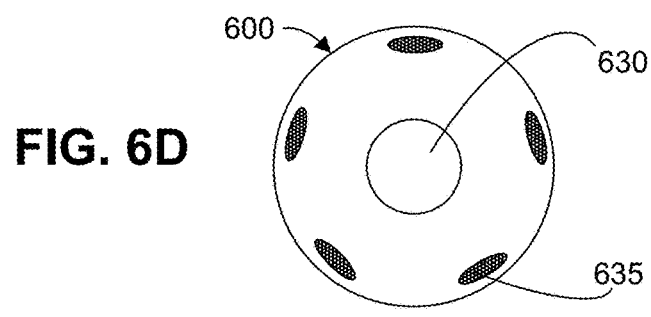

FIG. 6D shows five tear-film-sensitive sensors 635 disposed around eye-mountable device 600. As shown, FIG. 6D has an odd number of tear-film-sensitive sensors 635 spaced evenly around the periphery of eye-mountable device 600.

Figure 6E:
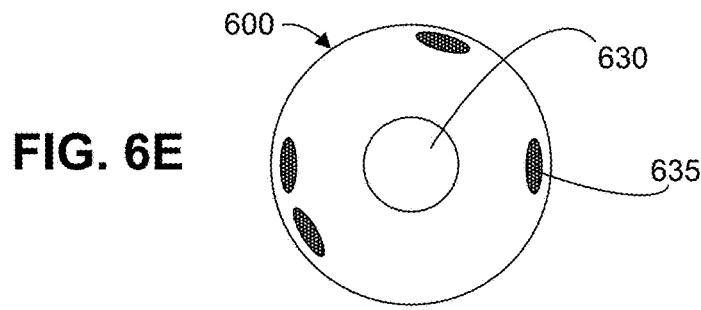

FIG. 6E shows four tear-film-sensitive sensors 635 disposed around eye-mountable device 600. The tear-film-sensitive sensors 635 are disposed unevenly around the periphery of the device. In some situations, non-symmetrical sensor configurations may be advantageous to detect the specific location/orientation of the lens.

Figure 7:
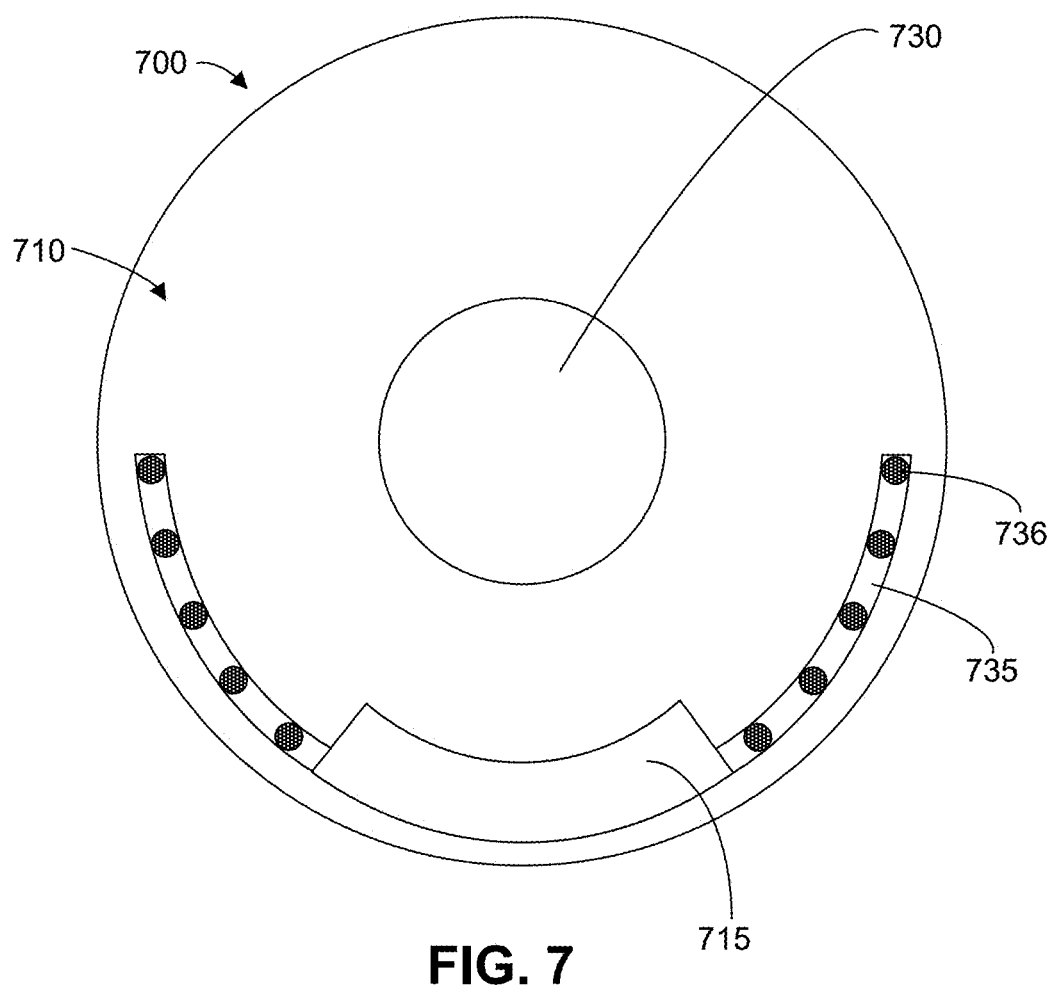
FIG. 7 illustrates a configuration of an eye-mountable device with a tear-film sensor system, in accordance with several embodiments of the disclosure.

Although FIGS. 6A-6E show configurations of tear-film-sensitive sensors 635 with 2, 3, 4, and 5 tear-film-sensitive sensors 635 disposed in the device, one skilled in the art will appreciate that other embodiments may have any number of tear-film-sensitive sensors 635 disposed in any configuration on eye-mountable device 600 (see infra FIG. 7). Different configurations may be advantageous in different eye-mountable device 600 use cases (e.g., a device that has various sensor systems for monitoring body chemistry may warrant a different tear-film-sensitive sensor 635 configuration than a device for active accommodation).

FIG. 7 illustrates a configuration of eye-mountable device 700 with a tear-film sensor system, in accordance with several embodiments of the disclosure. In the depicted embodiment, one or more tear-film-sensitive sensors 735 include at least two electrodes with multiple exposure regions 736 partially exposed (outside of enclosure 710) to contact the tear-film. The two electrodes partially encircle an accommodation actuator 730 and are coupled to, and/or disposed on, substrate 715 (although not depicted, substrate 715 may also house a controller, power supply, etc.). This alternate implementation has several openings over a single electrode (one electrode shown on the left, and one electrode shown on the right). Having multiple openings on a single electrode enables "discrete" steps in measured impedance. The measurement surface area is distributed over the multiple openings and does not need multiple discrete electrodes, which reduces the total number of electrical connections.

In many embodiments, (including those depicted in FIGS. 1-6) the one or more tear-film-sensitive sensors 735 include metal electrodes (e.g., platinum, platinum/iridium alloys, iridium, gold, or titanium). Sometimes, a conductive coating material (such as conductive polymer Nafion, PEDOT or high water content materials such as a silicone hydrogel) is disposed between the metal electrodes and the tear-film (to improve coupling with the tear film, minimize electrode fouling and allow for accurate impedance measurements).

Figure 8:
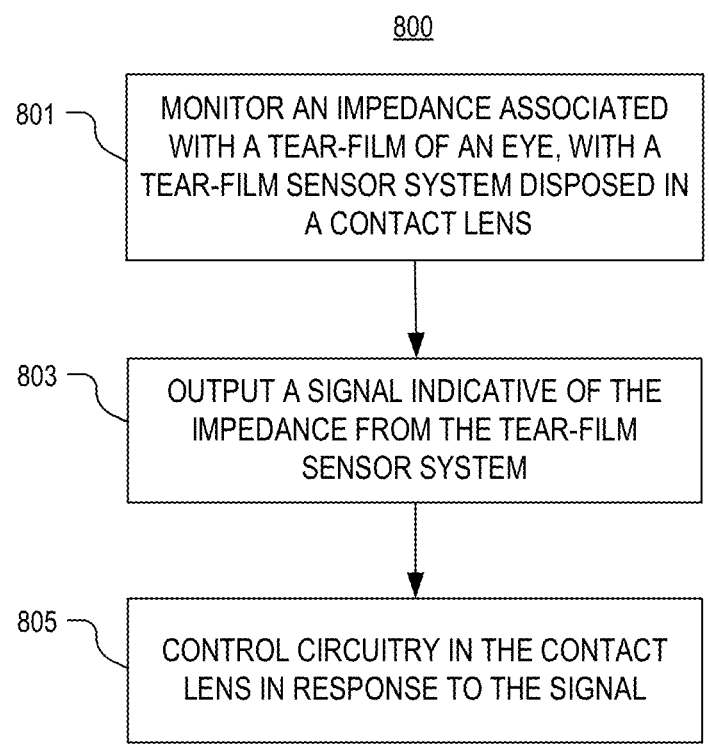
FIG. 8 illustrates a method of gaze detection, in accordance with an embodiment of the disclosure.

FIG. 8 is a flow chart illustrating a method 800 for gaze detection, in accordance with an embodiment of the disclosure. The order in which some or all of the method blocks appear should not be deemed limiting. Rather, one of ordinary skill in the art having the benefit of the present disclosure will understand that some of the method blocks may be executed in a variety of orders not illustrated, or even in parallel. Additionally, blocks may be added to, or excluded from, method 800, in accordance with embodiments of the disclosure.

Block 801 discloses monitoring an impedance associated with a tear-film of an eye using a tear-film sensor system disposed in a contact lens. The tear-film sensor system is disposed proximate to a periphery of the contact lens and measures the impedance across a surface of the contact lens. The impedance is influenced by the tear-film of the eye and an orientation of the eye. As stated, the tear-film is thicker in certain portions of the eye; thicker portions of tear-film result in a lower impedance because a greater amount of conducting fluid is disposed between one or more electrodes measuring the impedance. In other words, the impedance across the surface of the contact lens may change in response to changes in the volumetric conduction path through the tear film. In one embodiment, the tear-film sensor system applies an alternating current signal across a surface of the contact lens, and the alternating current signal is in a frequency range of 1 kHz to 1 MHz.

Block 803 shows outputting a signal indicative of the impedance from the tear-film sensor system; this signal may show the orientation of the eye. In one or more embodiments the orientation of the eye includes gaze directions including at least one of a downward gaze, an upward gaze, a sideways gaze, or a squint. The signal may include sub-signals corresponding to each of the gaze directions Block 805 illustrates controlling circuitry in the contact lens in response to the signal. In one embodiment, an accommodation actuator is disposed in contact lens to optically align with a cornea of the user when the eye-mountable device is mounted on the eye of the user. In this embodiment, the signal includes gaze detection information determined from changes to the impedance of the tear-film, and the controller controls a focus of the accommodation actuator in response to the signal. Thus, the focus of the lens can be changed based on determined directions of user viewing. In other embodiments, other components in the lens may be controlled. In one embodiment, gaze detection may be used as a method of manual communication with the contact lens. For example, the contact lens may measure a user's glucose, and alert the user to either a low glucose or high glucose condition. The user may acknowledge the signal by looking upward in rapid succession three times (or any other identifiable eye-movement pattern—such as blinking). However, this disclosure should not be limited to the use-cases disclosed. One skilled in the art will appreciate that there are many reasons gaze detection is useful in association with a contact lens (e.g., allowing disabled people to communicate via eye movement, accurately determining where people look for purposes of creating visually pleasing user interfaces, etc.).

In one embodiment, the contact lens has at least four impedance sensing electrodes and a comparison of the measured impedance levels across different electrode pairs is indicative of the lens's orientation on the eye. This measurement and comparison can be executed at pre-set intervals (for example after every blink) to assess the current contact lens orientation, and select the appropriate electrode pair (e.g., the pair in the temporo-nasal band of high impedance) from which to base algorithmic lens actuation. This may be used to achieve orientation independent sensing.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An eye-mountable device, comprising:
   an enclosure shaped to be removably mounted over a cornea of an eye of a user;
   a tear-film sensor system, including at least a first pair and a second pair of tear-film-sensitive sensors to measure an impedance across the eye-mountable device associated with a tear-film of the eye when the eye-mountable device is mounted on the eye of the user, wherein the tear-film sensor system is configured to alternately output a first and a second alternating current (AC) signal to measure the impedance, wherein the first AC signal is between the first pair of the tear-film-sensitive sensors disposed on opposite sides of the eye-mountable device from one another, and wherein the second AC signal is between the second pair of the tear-film-sensitive sensors disposed on opposite sides of the eye-mountable device from one another; and
   a controller disposed within the enclosure and coupled to the tear-film sensor system, wherein the controller includes instructions that when executed by the controller causes the eye-mountable device to perform operations including:
      monitoring the impedance across the eye-mountable device based, at least in part, on the alternately outputted first and second AC signals, wherein the impedance is influenced by the tear-film of the eye and an orientation of the eye; and
      determining a gaze direction of the eye based, at least in part, on the impedance and, in response to changes in the impedance, actively controlling circuitry disposed in the eye-mountable device.

2. The eye-mountable device of claim 1, wherein the orientation of the eye corresponds to a position of the eye of the user and a direction of user viewing.

3. The eye-mountable device of claim 1, further comprising:
   an accommodation actuator disposed in the eye-mountable device to optically align with a cornea of the user when the eye-mountable device is mounted on the eye of the user, and wherein the controller includes additional instructions that when executed by the controller causes the eye-mountable device to perform further operations including:
      adjusting a focus of the accommodation actuator in response to the changes of the impedance across the eye-mountable device.

4. The eye-mountable device of claim 1, wherein the eye-mountable device is a circular shape, wherein the first pair and the second pair of the tear-film-sensitive sensors are disposed around a periphery of the eye-mountable device such that light entering the eye is substantially unobstructed by the tear-film-sensitive sensors when the enclosure is mounted over the cornea.

5. The eye-mountable device of claim 4, wherein the tear-film sensor system includes an even number of tear-film-sensitive sensors, including the first and second pairs of tear-film-sensitive sensors, spaced evenly around the periphery of the eye-mountable device.

6. The eye-mountable device of claim 4, wherein the tear-film sensor system includes an odd number of the tear-film-sensitive sensors, including the first and second pairs, spaced evenly around the periphery of the eye-mountable device.

7. The eye-mountable device of claim 4, wherein the tear-film-sensitive sensors are unevenly spaced around the periphery of the eye-mountable device.

8. The eye-mountable device of claim 4, wherein the each of the first and the second pairs of the tear-film-sensitive sensors includes at least two electrodes with multiple exposure regions partially exposed to contact the tear-film.

9. The eye-mountable device of claim 1, wherein at least one of the tear-film-sensitive sensors include an electrode exposed to the tear-film, wherein the electrode includes metal.

10. A contact lens, comprising:
    a tear-film sensor system disposed within the contact lens to measure an impedance across the contact lens associated with a tear-film of an eye when the contact lens is mounted on the eye of a user, wherein the tear-film sensor system is configured to alternately output a first and a second alternating current (AC) signal to measure the impedance, wherein the first AC signal is between a first pair of tear-film-sensitive sensors disposed on opposite sides of the contact lens from one another, and wherein the second AC signal is between a second pair of tear-film-sensitive sensors disposed on opposite sides of the contact lens from one another;
    an accommodation actuator disposed in the contact lens to optically align with a cornea of the user when the contact lens is mounted on the eye; and
    a controller, disposed in the contact lens, electrically coupled to the tear-film sensor system and the accommodation actuator, wherein the controller includes instructions that when executed by the controller causes the contact lens to perform operations including:
       monitoring the impedance across the contact lens based, at least in part, on the alternately outputted first and second AC signals, wherein the impedance across the contact lens is influenced by the tear-film of the eye and an orientation of the eye;
       controlling one or more other pieces of circuitry disposed in the contact lens in response to the impedance; and
       electrically manipulating the accommodation actuator to change an optical power of the contact lens in response to a change in the impedance corresponding to a change in the orientation of the eye.

11. The contact lens of claim 10, wherein the impedance is proportional to a thickness of the tear-film.

12. The contact lens of claim 10, wherein the orientation of the eye includes gaze directions including at least one of a downward gaze, an upward gaze, a sideways gaze, or a squint.

13. The contact lens of claim 10, wherein the first and second pairs of tear-film-sensitive sensors include metal electrodes disposed proximate to a periphery of the contact lens.

14. The contact lens of claim 13, wherein the metal electrodes of the first and second pairs of tear-film-sensitive sensor are coated with a conductive material to mitigate fouling of the metal electrodes from exposure to the tear-film.

15. A method of gaze detection for an eye-mountable device, comprising:
alternately outputting a first and a second alternating current (AC) signal to measure impedance across the eye-mountable device associated with a tear-film of an eye when the eye-mountable device is mounted on the eye of a user, wherein the first AC signal is between a first pair of tear-film-sensitive sensors disposed on opposite sides of the eye-mountable device from one another, and wherein the second AC signal is between a second pair of tear-film-sensitive sensors disposed on opposite sides of the contact lens from one another;
monitoring the impedance across the eye-mountable device based, at least in part, on the first and second AC signals, wherein the impedance across the eye-mountable device is influenced by the tear-film of the eye and an orientation of the eye;
outputting a signal based, at least in part, on the impedance to indicate the orientation of the eye; and
controlling circuitry of the eye-mountable device in response to the signal.

16. The method of claim 15, wherein the orientation of the eye includes gaze directions including at least one of a downward gaze, an upward gaze, a sideways gaze, or a squint, and wherein the signal includes sub-signals corresponding to each of the gaze directions.

17. The method of claim 16, further comprising adjusting a focus of an accommodation actuator disposed in the eye-mountable device in response to the signal.

18. The method of claim 17, wherein the impedance across the eye-mountable device changes in response to a thickness of the tear-film.

19. The method of claim 18, further comprising:
comparing the impedance between pairs of tear-film-sensitive sensors, including the first pair and the second pair corresponding to at least four impedance sensing electrodes disposed on the eye-mountable device, to determine an orientation of the eye-mountable device on the eye.

20. The method of claim 15, further comprising:
determining horizontal and vertical orientation information of the eye-mountable device, wherein the impedance measured by the first and second pairs of tear-film-sensitive sensors indicate the horizontal and vertical orientation information, respectively.

21. The method of claim 17, further comprising: controlling the accommodation actuator based, at least in part, on the impedance measured between the first and second pair of the tear-film-sensitive sensors.

* * * * *